US012762821B2

(12) United States Patent
Kamon

(10) Patent No.: US 12,762,821 B2
(45) Date of Patent: Oct. 13, 2026

(54) MEDICAL IMAGE PROCESSING DEVICE, METHOD OF OPERATING MEDICAL IMAGE PROCESSING DEVICE, NON-TRANSITORY COMPUTER READABLE MEDIUM, AND ENDOSCOPE SYSTEM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 316 days.

(21) Appl. No.: 18/664,261

(22) Filed: May 14, 2024

(65) Prior Publication Data

US 2024/0386692 A1 Nov. 21, 2024

(30) Foreign Application Priority Data

May 16, 2023 (JP) ................................ 2023-080678

(51) Int. Cl.

| | |
|---|---|
| ***G06K 9/00*** | (2022.01) |
| ***A61B 1/00*** | (2006.01) |
| ***G06T 7/00*** | (2017.01) |
| ***G06V 10/25*** | (2022.01) |
| ***G06V 10/764*** | (2022.01) |

(52) U.S. Cl.

CPC ........ *G06V 10/25* (2022.01); *A61B 1/000096* (2022.02); *G06T 7/0012* (2013.01); *G06V 10/764* (2022.01); *G06T 2207/10068* (2013.01); *G06T 2207/20081* (2013.01); *G06T 2207/30096* (2013.01); *G06V 2201/031* (2022.01)

(58) Field of Classification Search

CPC ................ G06V 10/25; G06V 10/764; G06V 2201/031; A61B 1/000096; G06T 7/0012; G06T 2207/10068; G06T 2207/20081; G06T 2207/30096

See application file for complete search history.

(56) References Cited

U.S. PATENT DOCUMENTS

| | | | | |
|---|---|---|---|---|
| 11,995,821 | B2 * | 5/2024 | Jiang | G06T 7/0012 |
| 2021/0106209 | A1 * | 4/2021 | Usuda | A61B 1/0005 |
| 2021/0343011 | A1 | 11/2021 | Kamon | |
| 2022/0020496 | A1 * | 1/2022 | Saito | G06T 7/0012 |

FOREIGN PATENT DOCUMENTS

| | | |
|---|---|---|
| JP | 2022137276 | 9/2022 |
| WO | 2020162275 | 8/2020 |

* cited by examiner

*Primary Examiner* — Avinash Yentrapati
(74) *Attorney, Agent, or Firm* — JCIPRNET

(57) ABSTRACT

A medical image processing device includes a medical image acquisition unit that acquires a medical image, a region classification unit that classifies a region of a subject into a first region or a second region, and a region-of-interest detection unit that detects a region of interest from the medical image. The region-of-interest detection unit detects the region of interest using a first trained model obtained from machine learning with a first data set including data of the first region and data of the second region or a second trained model obtained from machine learning with a second data set including the data of the second region.

13 Claims, 13 Drawing Sheets

MEDICAL IMAGE PROCESSING DEVICE, METHOD OF OPERATING MEDICAL IMAGE PROCESSING DEVICE, NON-TRANSITORY COMPUTER READABLE MEDIUM, AND ENDOSCOPE SYSTEM

CROSS-REFERENCE TO RELATED APPLICATIONS

This application claims priority under 35 U.S.C § 119 (a) to Japanese Patent Application No. 2023-080678 filed on 16 May 2023. The above application is hereby expressly incorporated by reference, in its entirety, into the present application.

BACKGROUND OF THE INVENTION

1. Field of the Invention

The present invention relates to a medical image processing device, a method of operating the medical image processing device, a non-transitory computer readable medium, and an endoscope system.

2. Description of the Related Art

In a medical field, time-series medical images that are acquired by an endoscope system, an ultrasound diagnostic system, or the like and have been subjected to various types of image processing are used in a case where a medical doctor observes or diagnoses medical images. A medical image processing device disclosed in WO2020/162275A (corresponding to US2021/0343011A1) acquires region information indicating a region in a living body in an acquired medical image, and performs recognition processing, such as the detection of a region of interest, on the medical image. Any one of a plurality of trained models corresponding to the region information trained with deep learning or the like is used in the recognition processing. These trained models are models trained with image sets in which each region in the living body is imaged depending on a target region. Further, WO2020/162275A discloses that a display device is caused to display a result of detecting a region of interest in an aspect corresponding to an imaged region.

A processor device (medical image processing device) disclosed in JP2022-137276A also recognizes an imaged region of a living body shown in an acquired medical image, and further performs recognition processing for acquiring information corresponding to the imaged region on the medical image. Trained models, which are trained with deep learning or the like, are used for these types of recognition processing.

SUMMARY OF THE INVENTION

As disclosed in WO2020/162275A and JP2022-137276A, the trained models used for the recognition processing and the like corresponding to the region information are models trained with an image set including medical images in which a target region in a living body is imaged. In a case where acquired region information is incorrect or a medical doctor who is a user inputs region information by mistake, recognition processing is performed by a trained model based on an image set including medical images of a region different from the actual region. In a case where the recognition processing is performed by a trained model based on an image set of a region different from the actual region as described above, false detection may frequently occur, or an unstable behavior that detects a region that is actually not a region of interest as the region of interest or detects an actual region of interest as a region that is not the region of interest, and the like may occur.

An object of the present invention is to provide a medical image processing device that can prevent false detection in detection processing corresponding to region information to perform stable detection, a method of operating the medical image processing device, a non-transitory computer readable medium, and an endoscope system.

A medical image processing device according to an aspect of the present invention comprises a processor. The processor is configured to: acquire a medical image in which a subject is imaged; classify a region of the subject of the medical image into a first region or a second region; and detect a region of interest from the medical image using a first trained model obtained from machine learning with a first data set including data of the first region and data of the second region with regard to the medical image of which the region of the subject is classified into the first region, and detect a region of interest from the medical image using a second trained model obtained from machine learning with a second data set including the data of the second region with regard to the medical image of which the region of the subject is classified into the second region. The first data set includes the data of the first region more than the data of the second region.

It is preferable that the first trained model has detection accuracy of the region of interest in the first region higher than the detection accuracy of the region of interest in the second region, and the second trained model has the detection accuracy of the region of interest in the second region higher than detection accuracy of the region of interest in the first region.

It is preferable that the first data set includes an image including the region of interest and an image not including the region of interest that correspond to the data of the first region and an image not including the region of interest that corresponds to the data of the second region.

It is preferable that the first trained model or the second trained model is the trained model trained with data and/or the first data set or the second data set having different combinations of the data.

It is preferable that the processor analyzes the medical image to acquire a classification result indicating the region of the subject in which the medical image is captured, and selects the first trained model or the second trained model corresponding to the classification result.

It is preferable that the processor acquires a classification result indicating the region of the subject in which the medical image is captured on the basis of a user's input, and selects the first trained model or the second trained model corresponding to the classification result.

It is preferable that the processor performs a control of notifying a user of a detection result obtained from the first trained model or the second trained model. It is preferable that the processor performs a display control of causing a medical image display to display the acquired time-series medical images, and causes the medical image display to display the medical images in which the region of interest is detected such that the detection result is superimposed on the medical images, for the notification.

It is preferable that the processor notifies a user of not only the detection result but also a selection state of the first trained model or the second trained model. It is preferable that the machine learning is deep learning.

An endoscope system according to another aspect of the present invention comprises an endoscope that captures the medical image; and the medical image processing device.

A method of operating a medical image processing device according to still another aspect of the present invention comprises: a step of acquiring a medical image in which a subject is imaged; a step of classifying a region of the subject in which the medical image is captured into a first region or a second region; a step of detecting a region of interest from the medical image using a first trained model obtained from machine learning with a first data set including data of the first region and data of the second region with regard to the medical image of which the region of the subject is classified into the first region; and a step of detecting a region of interest from the medical image using a second trained model obtained from machine learning with a second data set including the data of the second region with regard to the medical image of which the region of the subject is classified into the second region. The first data set includes the data of the first region more than the data of the second region.

A non-transitory computer readable medium storing a computer-executable program according to yet another aspect of the present invention causes a computer to execute: processing for acquiring a medical image in which a subject is imaged; processing for classifying a region of the subject in which the medical image is captured into a first region or a second region; and processing for detecting a region of interest from the medical image using a first trained model obtained from machine learning with a first data set including data of the first region and data of the second region with regard to the medical image of which the region of the subject is classified into the first region; and processing for detecting a region of interest from the medical image using a second trained model obtained from machine learning with a second data set including the data of the second region with regard to the medical image of which the region of the subject is classified into the second region. The first data set includes the data of the first region more than the data of the second region.

According to the present invention, it is possible to prevent false detection in detection processing corresponding to region information to perform stable detection.

BRIEF DESCRIPTION OF THE DRAWINGS

FIG. 7A is a diagram illustrating a case where a first data set is input, and FIG. 7B is a diagram illustrating a case where a second data set is input.

FIG. 9A is a diagram illustrating a case where the stomach is recognized as a classification result for a region, and FIG. 9B is a diagram illustrating a case where the esophagus is recognized as a classification result for a region.

DESCRIPTION OF THE PREFERRED EMBODIMENTS

First Embodiment

Figure 1:
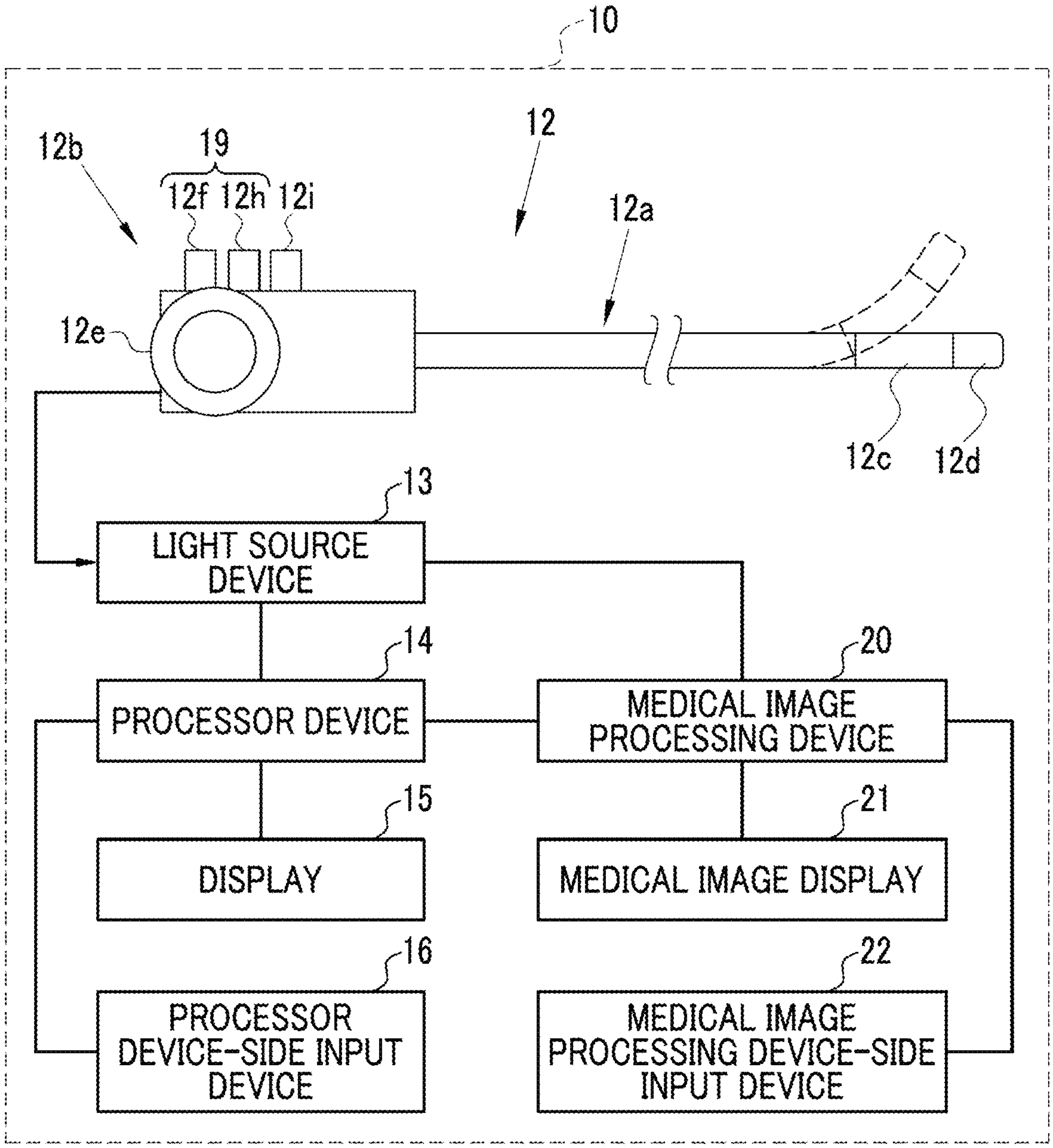
FIG. 1 is a schematic diagram of an endoscope system.

As shown in FIG. 1, a medical image processing device 20 according to an embodiment of the present invention is included in an endoscope system 10. The endoscope system 10 images an object to be observed to acquire medical images, such as endoscopic images.

The endoscope system 10 comprises an endoscope 12, a light source device 13, a processor device 14, a display 15, a processor device-side input device 16, the medical image processing device 20, a medical image display 21, and a medical image processing device-side input device 22. The endoscope 12 is optically or electrically connected to the light source device 13 and is electrically connected to the processor device 14. The medical image processing device 20 is electrically connected to the light source device 13 and the processor device 14.

The endoscope 12 includes an insertion part 12*a*, an operating part 12*b*, a bendable part 12*c*, and a distal end part 12*d*. The insertion part 12*a* is inserted into the body of an examinee. The operation part 12*b* is provided at a proximal end portion of the insertion part 12*a*. The bendable part 12*c* and the distal end part 12*d* are provided on a distal end side of the insertion part 12*a*. The bendable part 12*c* is operated to be bent in a case where angle knobs 12*e* of the operation part 12*b* are operated. As the bendable part 12*c* is operated to be bent, the distal end part 12*d* is made to face in a desired direction.

An imaging optical system for forming an image of a subject and an illumination optical system for irradiating the subject with illumination light are provided in the endoscope 12. The operation part 12*b* is provided with angle knobs 12*e*, a mode selector switch 12*f*, a still image acquisition instruction switch 12*h*, and a zoom operation part 12*i*. The mode selector switch 12*f* is used for an operation for switching an observation mode. The still image acquisition instruction switch 12*h* is used for an instruction for acquiring a still image of the subject. The zoom operation part 12*i* is used for an operation for enlarging or reducing an object to be observed. The operation part 12*b* may be provided with a scope-side input device 19, which is used to perform various operates on the processor device 14, in addition to the mode selector switch 12*f* and the still image acquisition instruction switch 12*h*.

The light source device 13 generates illumination light. The processor device 14 performs a system control on the endoscope system 10 and further performs image processing or the like on image signals transmitted from the endoscope 12 to generate medical images, and the like. The processor device 14 transmits the medical images to the medical image processing device 20 in addition to the display 15. The display 15 displays an operation image and the like in addition to the medical images transmitted from the processor device 14. The processor device-side input device 16 includes a keyboard, a mouse, a foot switch, a touch pen, and the like, and receives an input operation, such as function settings made by a user.

The medical image processing device 20 is connected to the medical image display 21. The medical image processing device 20 receives the medical images transmitted from the processor device 14, and performs various types of processing on the basis of the received medical images. The medical image processing device 20 transmits results of the various types of processing to the medical image display 21 in addition to the medical images. The medical image display 21 displays the medical images and the like transmitted from the medical image processing device 20.

The endoscope system 10 has a normal mode, a region-of-interest detection mode, and a region classification mode. In the normal mode, a color normal image obtained in a state where an object to be observed is irradiated with white light is displayed on the display 15 as the medical images. In the region classification mode, region classification processing is performed on the medical images and detector selection processing for selecting a region-of-interest detector corresponding to a classification result is performed. Further, in the region classification mode, the types and the like of classified regions are displayed on the medical image display 21 as necessary. In the region-of-interest detection mode, in a case where region-of-interest detection processing is performed on the medical images and a region of interest is detected, the medical image display 21 displays that the region of interest is present.

The normal mode, the region-of-interest detection mode, and the region classification mode described above can be set by the medical image processing device-side input device 22. With regard to the setting of the mode, two or more modes can also be simultaneously executed (for example, all the region classification mode and the region-of-interest detection mode can also be executed) in addition to the sequential switching of the modes. The details of the region classification mode and the region-of-interest detection mode to be executed by the medical image processing device 20 will be described later.

Figure 2:
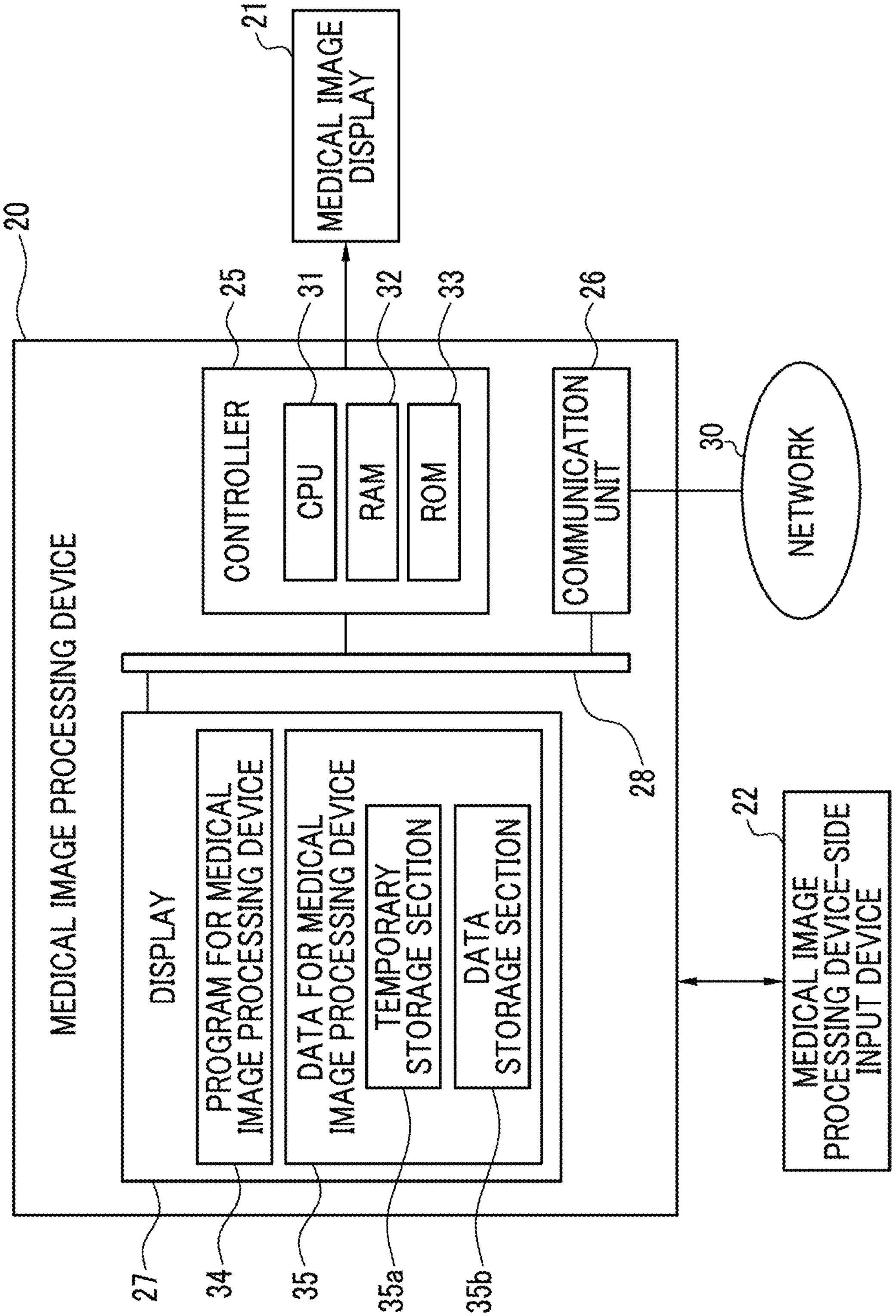
FIG. 2 is a block diagram illustrating a configuration of a medical image processing device.

As shown in FIG. 2, the medical image processing device 20 according to the present embodiment is a computer in which a controller 25, a communication unit 26, and a storage unit 27 are electrically connected to each other via a data bus 28 as a hardware configuration. The medical image display 21 and the medical image processing device-side input device 22 described above are connected to the medical image processing device 20. Further, the medical image processing device 20 comprises a speaker 29 that is used to notify a user.

The medical image processing device-side input device 22 is an input device having the same configuration as the above-mentioned processor device-side input device 16, that is, including a keyboard, a mouse, a foot switch, and the like. The present invention is not limited thereto, and a touch panel provided in the medical image display 21, the scope-side input device 19 of the endoscope 12, and/or the like may be included in the medical image processing device-side input device 22. Alternatively, the processor device-side input device 16 and the medical image processing device-side input device 22 may be formed of a common input device, and the operation of the processor device 14 and the operation of the medical image processing device 20 may be switched and performed depending on the purpose of use or the situation of use.

A computer forming the medical image processing device 20 receives an input of various instructions from the medical image processing device-side input device 22. The medical image processing device 20 receives the medical images transmitted from the processor device 14, and performs various types of processing, such as region classification processing or region-of-interest detection processing, on the basis of the received medical images. The medical image processing device 20 transmits results of the various types of processing to the medical image display 21 in addition to the medical images. The medical image display 21 may display various operation screens corresponding to the operation of the medical image processing device-side input device 22 in addition to the medical images acquired from the processor device 14. For example, the operation screen has operation functions using a graphical user interface (GUI). The computer forming the medical image processing device 20 can receive an input from a user via the operation screen.

The controller 25 includes a central processing unit (CPU) 31 that is a processor, a random access memory (RAM) 32, a read only memory (ROM) 33, and the like. The CPU 31 loads a program stored in the storage unit 27 or the like into the RAM 32 or the ROM 33 and executes processing corresponding to the program to generally control each part of the computer. The communication unit 26 is a network interface that controls the transmission of various types of information via a network 30. The RAM 32 or the ROM 33 may have a function of the storage unit 27.

The storage unit 27 is an example of a memory and is, for example, a hard disk drive or a solid-state drive that is built in the computer forming the medical image processing device 20 or is connected to the computer via a cable or the network 30, or a disk array in which a plurality of hard disk drives or the like are continuously mounted. A control program, various application programs, various data to be used for these programs, display data of various operation screens attached to these programs, and the like are stored in the storage unit 27.

The storage unit 27 of the present embodiment stores various data, such as a program 34 for a medical image processing device and data 35 for a medical image processing device. The program 34 for a medical image processing device or the data 35 for a medical image processing device are a program or data that are used to realize various functions of the medical image processing device 20. The functions of the medical image processing device 20 are realized by the program 34 for a medical image processing device and the data 35 for a medical image processing device. The data 35 for a medical image processing device include, for example, a temporary storage section **35*a* that is a region in which data are temporarily stored and a data storage section 35*b*** in which data and the like of the program are stored.

The computer forming the medical image processing device 20 may be a general-purpose server device, a personal computer (PC), or the like in addition to a device designed exclusively. Further, it is sufficient that the functions of the medical image processing device 20 can be exhibited, the computer may also be shared with devices having other functions, or the functions of the medical image processing device 20 can also be incorporated into a processor device for an endoscope, a medical information management device, and/or the like. In the medical image processing device 20, programs relating to medical image processing are stored in the storage unit 27 that is a memory for a program.

Figure 3:
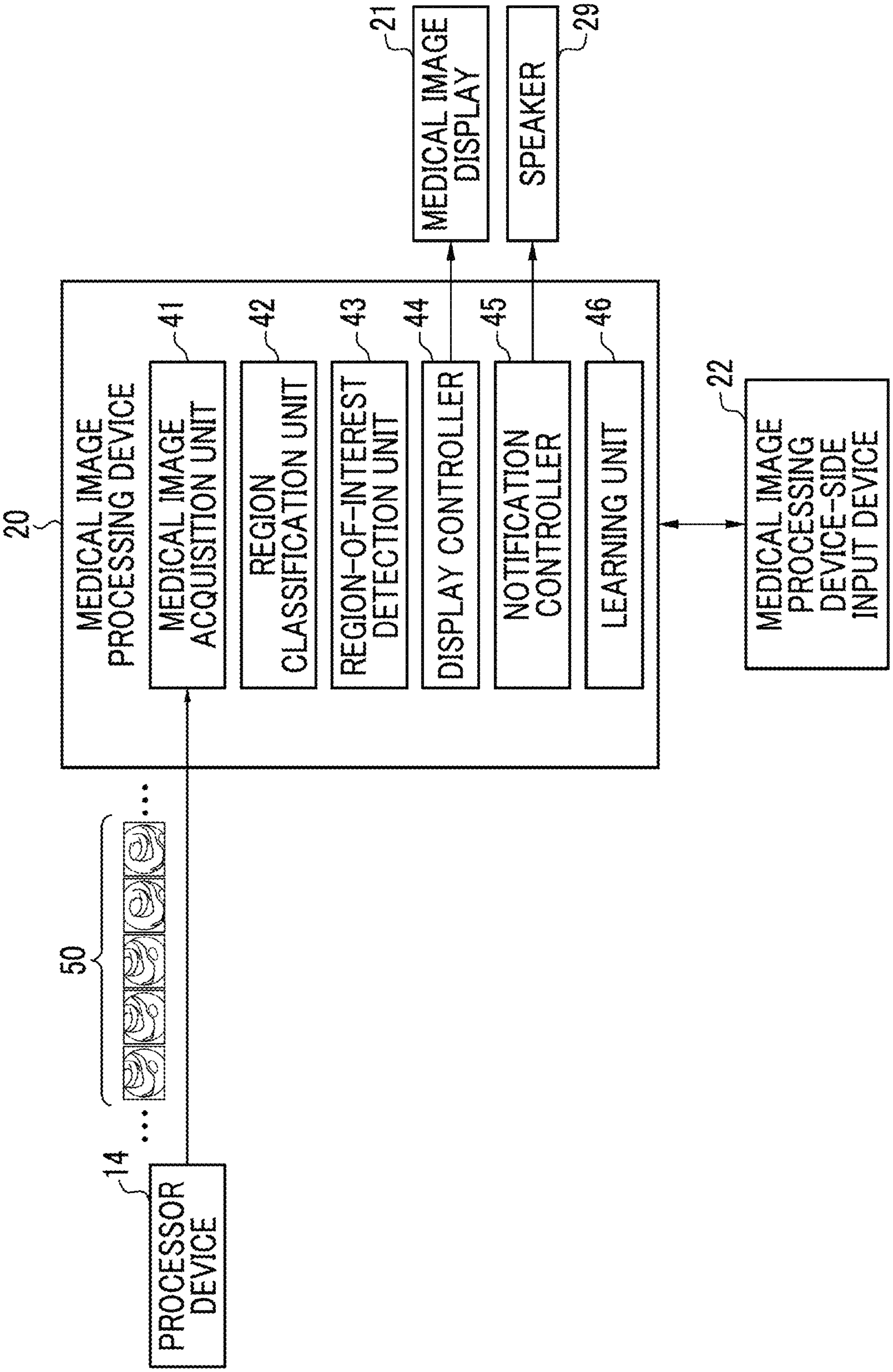
FIG. 3 is a block diagram showing functions of the medical image processing device.

As shown in FIG. 3, the program 34 for a medical image processing device stored in the storage unit 27 is operated by the controller 25 in the medical image processing device 20, so that the functions of a medical image acquisition unit 41, a region classification unit 42, a region-of-interest detection unit 43, a display controller 44, a notification controller 45, and a learning unit 46 are realized.

The medical image acquisition unit 41 sequentially acquires medical images from the processor device 14 to acquire a medical image in which a subject is imaged. In the present embodiment, the medical images acquired from the processor device 14 by the medical image acquisition unit 41 are a plurality of time-series medical images. In the present embodiment, an endoscopic image obtained by the endoscope 12 is acquired as the medical image. However, the medical image is not limited to an endoscopic image, and other images, such as an ultrasonic image, a computed tomography (CT) image, a magnetic resonance imaging (MRI) image, and the like, may be received.

The region classification unit 42 analyzes the medical images acquired by the medical image acquisition unit 41 to perform region classification processing for classifying a region of a subject in which the medical images are captured. The region-of-interest detection unit 43 performs detector selection processing for selecting a region-of-interest detector and region-of-interest detection processing for detecting a region of interest from the medical image with the selected region-of-interest detector, on the basis of the region classification processing performed by the region classification unit 42. Specific contents of the region classification processing, the detector selection processing, and the region-of-interest detection processing will be described later.

It is preferable that the region-of-interest detection processing or the region classification processing is processing performed by a trained model obtained from, for example, deep learning using a neural network (NN), a convolutional neural network (CNN), a recurrent neural network (RNN), or the like. Alternatively, learning is not limited to the deep learning, and the region-of-interest detection processing or the region classification processing may be processing performed by a trained model obtained from other machine learning, for example, learning using Adaboost or random forest.

A region of interest detected with the region-of-interest detection processing by the region-of-interest detection unit 43 is, for example, a region including a lesion area typified by a cancer, a treatment trace, a surgical scar, a bleeding site, a benign tumor area, and an inflammation area (including a portion with changes, such as bleeding or atrophy, in addition to so-called inflammation). That is, a region including a lesion, a region having a possibility of a lesion, or a region which is required to be observed in detail regardless of a possibility of a lesion, such as a dark region (the back of folds, a region where observation light is difficult to reach due to the deep lumen), or the like may be a region of interest. In the region-of-interest detection processing, a region including at least one of a lesion area, a benign tumor area, or an inflammation area is detected as the region of interest.

Further, in the region classification processing performed by the region classification unit 42, a region of a subject in which medical images 50 are captured is classified into a first region or a second region. In the region classification unit 42, a trained model, which has been trained with medical images as described above and generated, is used to recognize a plurality of preset regions of the subject including the first region and the second region. Then, in the region classification processing, the trained model is used to determine whether or not the first region or the second region is included in the medical images. In the region classification processing, the plurality of regions of the subject that are objects to examined are set depending on the purpose of an examination, or the like.

Figure 4:
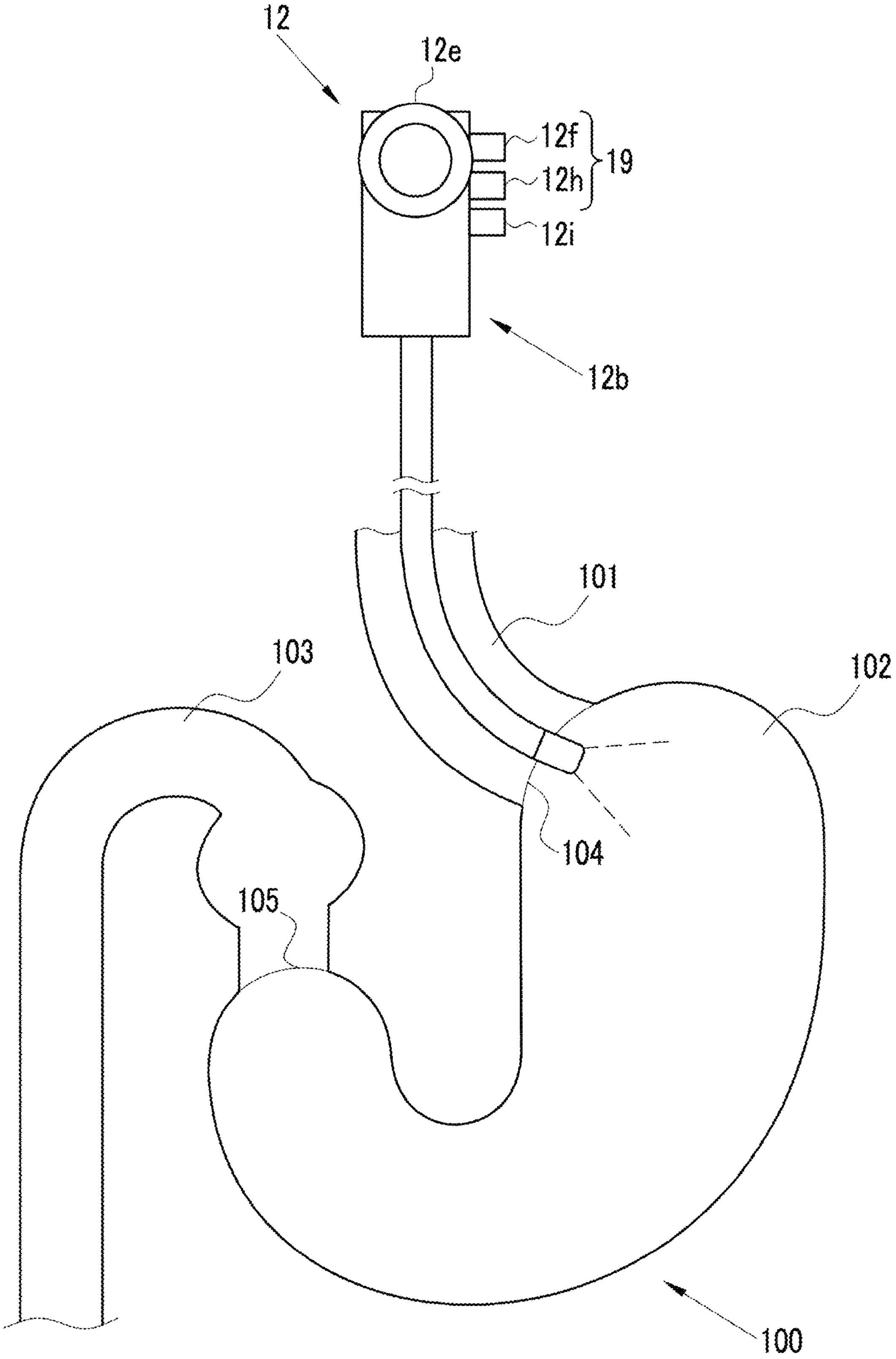
FIG. 4 is a diagram illustrating a state in which an examination is made using an endoscope system.

As shown in FIG. 4, in the present embodiment, the endoscope system 10 examines an upper gastrointestinal tract 100. That is, a case where an upper gastrointestinal tract 100 is imaged by the endoscope 12 and an esophagus 101, a stomach 102, and a duodenum 103 are set as a plurality of regions of the subject preset by the region classification unit 42 will be exemplified. As described above, any one of the plurality of regions of the subject preset by the region classification unit 42 corresponds to a "first region" and a "second region" in claims. The present invention is not limited thereto, and the plurality of regions of the subject preset by the region classification unit 42 may include at least the "first region" and the "second region" or may include three or more regions.

The present invention is not limited thereto, and an examination made by the endoscope system 10 may be, for example, the examination of another portion of the subject, such as the examination of a lower gastrointestinal tract. In the case of the examination of a lower gastrointestinal tract, for example, a large intestine and a small intestine are set as a plurality of preset regions of the subject. Further, in the region classification processing, smaller regions may be set as the preset regions of the subject. For example, in a case where the inside of the stomach is examined, a dome portion, an upper gastric body, a middle gastric body, a lower gastric body, a cardiac region, the stomach corner, and the like may be set as the preset regions of the subject. Further, in a case where the inside of the large intestine is examined, a rectum, a sigmoid colon, a descending colon, a transverse colon, and the like may be set as the preset regions of the subject.

Figure 5:
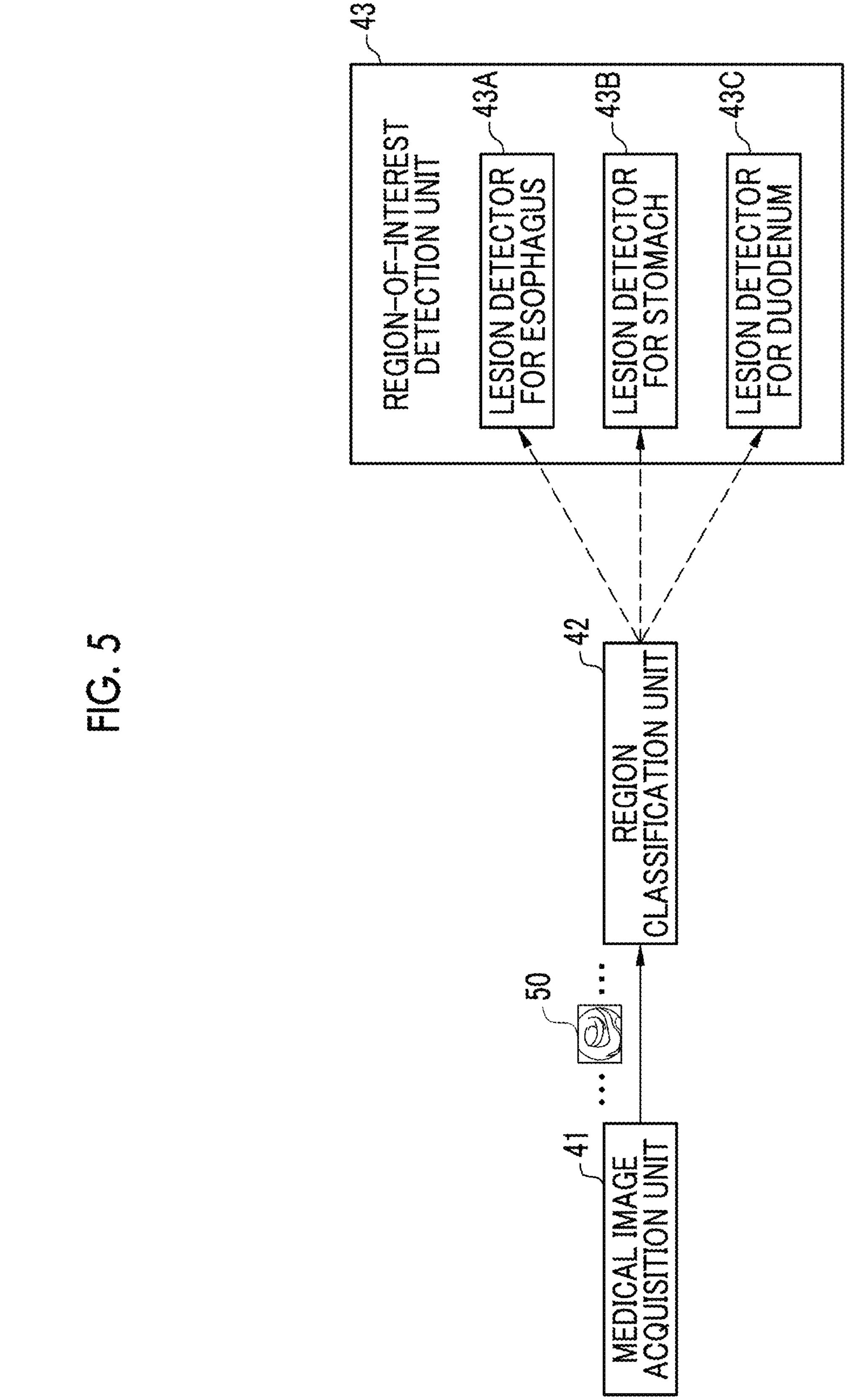
FIG. 5 is a diagram illustrating processing of a region classification unit and a region-of-interest detection unit.

As shown in FIG. 5, the medical images 50 acquired in a time series by the medical image acquisition unit 41 are input to the region classification unit 42. The region classification unit 42 performs the region classification processing using the medical images 50. As described above, the esophagus 101, the stomach 102, and the duodenum 103 are set as the plurality of preset regions of the subject in the present embodiment. That is, the region classification unit 42 analyzes the medical images 50 to perform the region classification processing for recognizing which region of the esophagus 101, the stomach 102, or the duodenum 103 is the region of the subject in which the medical images 50 are captured and classifying the region of the subject. A classification result obtained from the region classification processing performed by the region classification unit 42 and the medical images 50 subjected to the region classification processing are input to the region-of-interest detection unit 43.

The region-of-interest detection unit 43 includes a lesion detector 43A for an esophagus, a lesion detector 43B for a stomach, and a lesion detector 43C for a duodenum that are a plurality of region-of-interest detectors. The lesion detector 43A for an esophagus, the lesion detector 43B for a stomach, and the lesion detector 43C for a duodenum correspond to the esophagus 101, the stomach 102, and the duodenum 103 that are a plurality of preset regions of the subject, respectively.

The region-of-interest detection unit 43 acquires the classification result obtained from the region classification unit 42, and selects any one of the lesion detector 43A for an esophagus, the lesion detector 43B for a stomach, or the lesion detector 43C for a duodenum corresponding to the classification result. That is, in a case where the classification result of the classification of the medical images 50 performed by the region classification unit 42 is the esophagus 101, the region-of-interest detection unit 43 selects the lesion detector 43A for an esophagus. Likewise, in a case where the classification result is the stomach 102, the region-of-interest detection unit 43 selects the lesion detector 43B for a stomach. Likewise, in a case where the classification result is the duodenum 103, the region-of-interest detection unit 43 selects the lesion detector 43C for a duodenum. In this way, in a case where the region of the subject is classified into the first region, the region-of-interest detector to be selected by the region-of-interest detection unit 43 corresponds to a "first trained model". Likewise, in a case where the region of the subject is classified into the second region, the region-of-interest detector to be selected by the region-of-interest detection unit 43 corresponds to a "second trained model".

The region-of-interest detection unit 43 performs the region-of-interest detection processing for detecting a region of interest from the medical images 50 using any one of the lesion detector 43A for an esophagus, the lesion detector 43B for a stomach, or the lesion detector 43C for a duodenum selected in the detector selection processing. Information on the detected region of interest and the medical images 50 in which the region of interest is detected are input to the display controller 44. The display controller 44 performs a display control of causing the medical image display 21 to display the medical images 50 in a time series. Further, the display controller 44 notifies a user of a detection result in a case where the region of interest is detected.

The display controller 44 performs a display control of causing the medical image display 21 to display the medical images 50 that are acquired in a time series and subjected to the region classification processing and the region-of-interest detection processing, and performs a control of notifying a user of the detection result of the region of interest. It is preferable that the display controller 44 notifies a user of the detection result during an examination. Specifically, in a case where the time-series medical images 50 are displayed on the medical image display 21, the notification controller 45 causes the medical image display 21 to display the medical images 50 in which the region of interest is detected such that the detection result of the region of interest is superimposed on the medical images 50.

Figure 6:
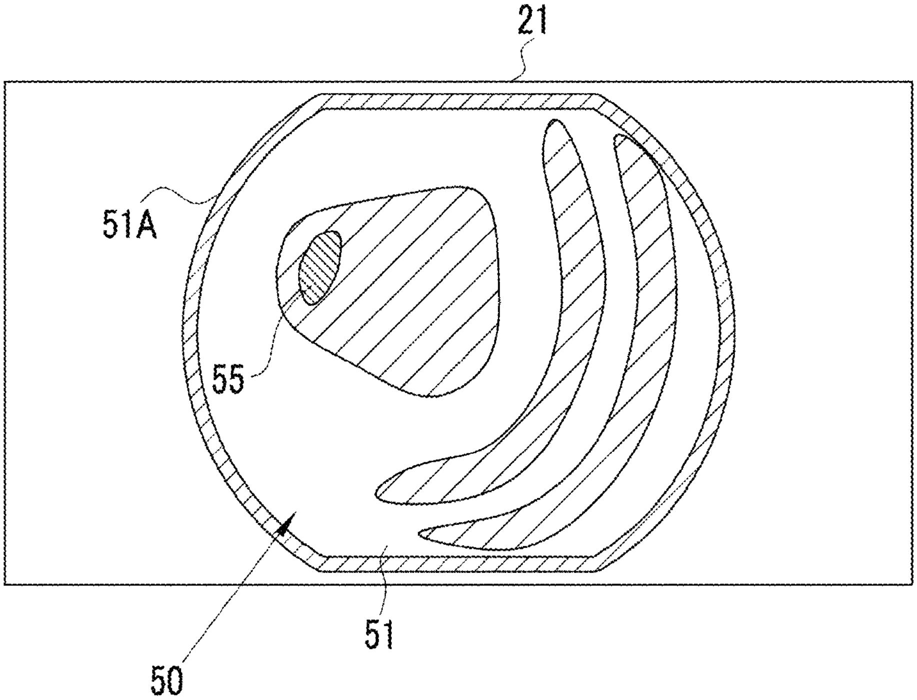
FIG. 6 is an image diagram showing a display aspect of a medical image display.

For example, in a case where a region 55 of interest is detected from the medical image 50 by the region-of-interest detection unit 43 as shown in FIG. 6, it is preferable that the display controller 44 highlights an outer frame 51A of a main screen 51, which displays the medical image 50 in real time as a video under examination, in a color for the notification of a detection result. Further, it is preferable that the color for the notification of a detection result is set to be different from a color in a case where a region of interest is not detected. For example, in a case where the color in a case where a region of interest is not detected is set to yellow, it is preferable that the color for the notification of a detection result is set to blue which is a complementary color to yellow.

Further, the notification of the detection result using the display controller 44 is not limited thereto, and a portion including the region 55 of interest in the medical image 50 displayed on the main screen 51 may be highlighted in a color different (a color having different shading, brightness, chroma saturation, or the like) from an actual color or a figure may be superimposed and displayed on a portion including the region 55 of interest or on the periphery of the region 55 of interest.

The notification controller 45 performs a control of notifying a user of the detection result of the region of interest with a method different from a method of displaying the medical image on the medical image display 21. For example, the notification controller 45 controls the speaker 29, and plays a notification sound from the speaker 29 in a case where the region of interest is detected from the medical image 50 by the region-of-interest detection unit 43. Further, for example, a notification sound is played from the speaker 29 according to highlighting for the notification of the detection result in the above-mentioned display controller 44.

The learning unit 46 generates the lesion detector 43A for an esophagus, the lesion detector 43B for a stomach, and the lesion detector 43C for a duodenum described above using deep learning. The lesion detector 43A for an esophagus, the lesion detector 43B for a stomach, and the lesion detector 43C for a duodenum are trained models that are obtained from deep learning performed by the learning unit 46. A configuration in which the region-of-interest detectors included in the region-of-interest detection unit 43 are generated by deep learning is not limited thereto, and trained models, which are generated in a case where the same deep learning as the deep learning performed by the learning unit 46 is performed by a device provided outside the medical image processing device 20, may be acquired and may be used as region-of-interest detectors. For example, an external cloud server, which is connected via the network 30, or the like may be caused to execute the same functions as the learning unit 46, and trained models, which have been subjected to deep learning by a learning unit on this cloud server, may be acquired by the medical image processing device 20 and may be used as a plurality of region-of-interest detectors included in the region-of-interest detection unit 43.

Figure 7A:
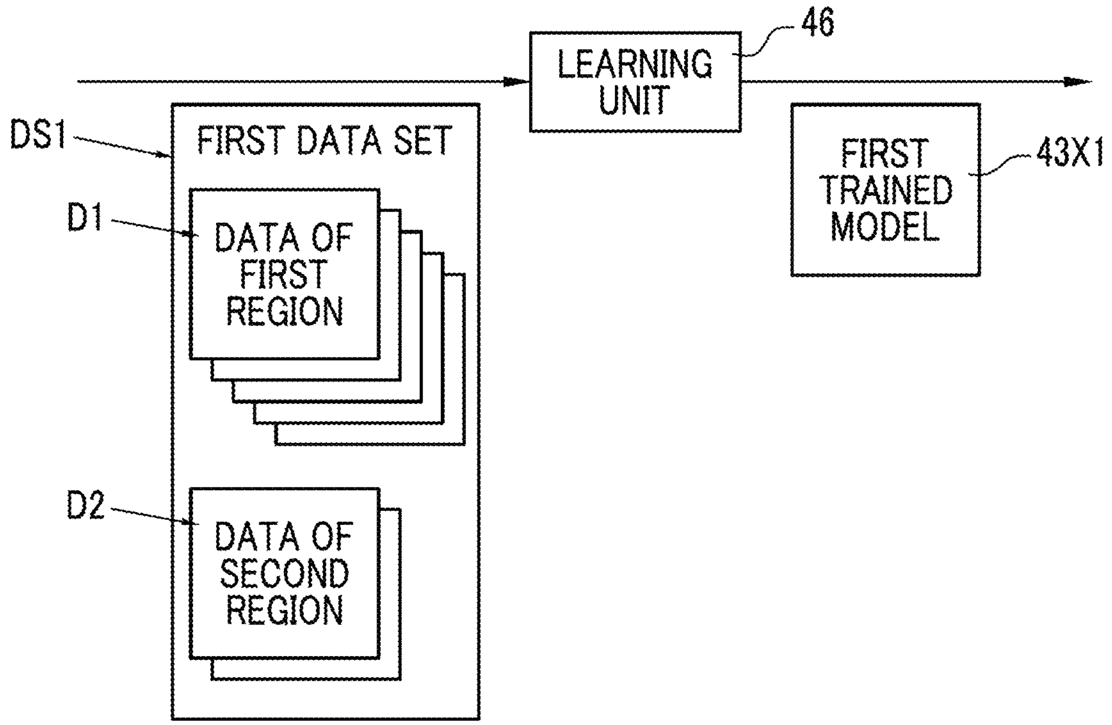
FIGS. 7A and 7B are diagrams illustrating learning for generating a trained model with a learning unit.
Figure 7B:
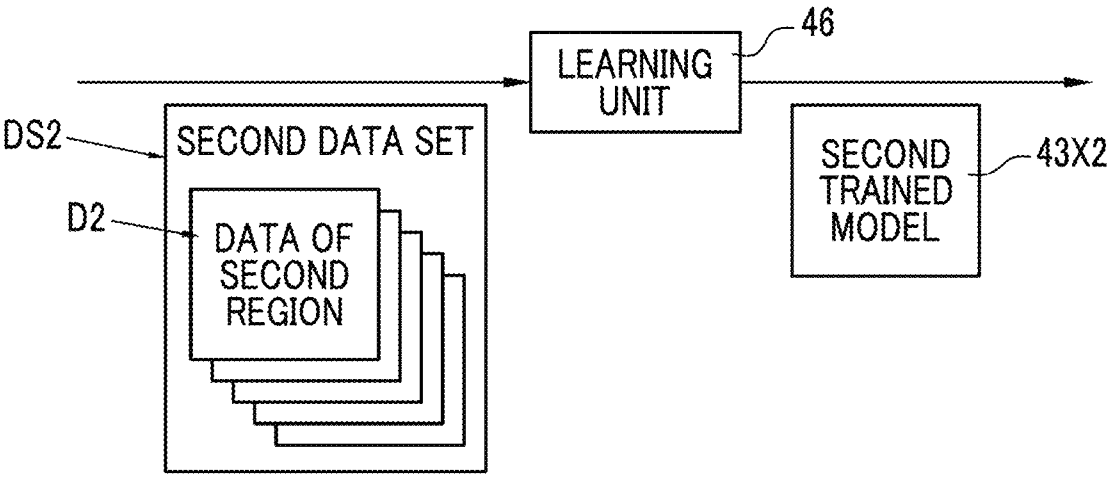

As shown in FIGS. 7A and 7B, a first data set DS1 or a second data set DS2 including a plurality of medical images is input to the learning unit 46 and the deep learning is performed by the learning unit 46. A first trained model 43X1, which is generated by the learning unit 46 and is used as any one of the lesion detector 43A for an esophagus, the lesion detector 43B for a stomach, or the lesion detector 43C for a duodenum, is a trained model that is obtained using the first data set DS1 from the above-mentioned deep learning. The first data set DS1 includes a plurality of data D1 of the first region and a plurality of data D2 of the second region. Specifically, the data D1 are the data of a medical image in which the first region is imaged, and the data D2 are the data of a medical image in which the second region is imaged.

The contents of the "first region" and the "second region" change depending on which one of the lesion detector 43A for an esophagus, the lesion detector 43B for a stomach, and the lesion detector 43C for a duodenum corresponds to the first trained model. Specifically, in a case where the first trained model is the lesion detector 43A for an esophagus, the “first region” is a region to which the lesion detector 43A for an esophagus corresponds, that is, the esophagus and the “second region” is a region of the plurality of preset regions of the subject except for the first region, that is, the stomach or the duodenum.

As shown in FIG. 7B, a second trained model 43X2 is a trained model that is obtained using the second data set DS2 from the above-mentioned deep learning. The second data set DS2 includes the plurality of data D2 of the second region. In a case where the first region is the esophagus and the second region is the stomach as in the above-mentioned specific example, the data D1 of the first region are the data of a medical image in which the esophagus is imaged and the data D2 of the second region are the data of a medical image in which the stomach is imaged.

Further, the second region may be the duodenum in the above-mentioned specific example. In this case, the data D2 of the second region are the data of a medical image in which the duodenum is imaged, and the second data set DS2 includes a plurality of data D2 of the second region, that is, the data of the medical image in which the duodenum is imaged.

Furthermore, in a case where the first trained model is the lesion detector 43B for a stomach, the “first region” is a region to which the lesion detector 43B for a stomach corresponds, that is, the stomach and the “second region” is a region of the plurality of preset regions of the subject except for the first region, that is, the esophagus or the duodenum. Further, in a case where the first trained model is the lesion detector 43C for a duodenum, the “first region” is the duodenum and the “second region” is a region of the plurality of preset regions of the subject except for the first region, that is, the stomach or the esophagus. Even in the cases described above, as in the above-mentioned specific example, the learning unit 46 performs deep learning using the first data set DS1 including the data D1 of the first region and the data D2 of the second region and the second data set DS2 including the data D2 of the second region, so that a first trained model and a second trained model are obtained.

As described above, the first data set DS1 or the second data set DS2 is input to the learning unit 46 and deep learning is performed to obtain the lesion detector 43A for an esophagus, the lesion detector 43B for a stomach, and the lesion detector 43C for a duodenum that are the first trained models or the second trained models.

The first data set DS1 includes the data D1 of the first region more than the data D2 of the second region. For example, in a case where the first region is the esophagus, the first data set DS1 includes the data of the esophagus, which are the data D1 of the first region, more than the data of the stomach or the duodenum that are the data D2 of the second region.

It is preferable that the lesion detector 43A for an esophagus, the lesion detector 43B for a stomach, and the lesion detector 43C for a duodenum are first trained models or second trained models trained with the data D1, the data D2, and/or a first data set DS1 or a second data set DS2 having different combinations of the data D1 and D2. Accordingly, a first trained model or a second trained model optimal for each of the lesion detector 43A for an esophagus, the lesion detector 43B for a stomach, and the lesion detector 43C for a duodenum is generated.

Figure 8:
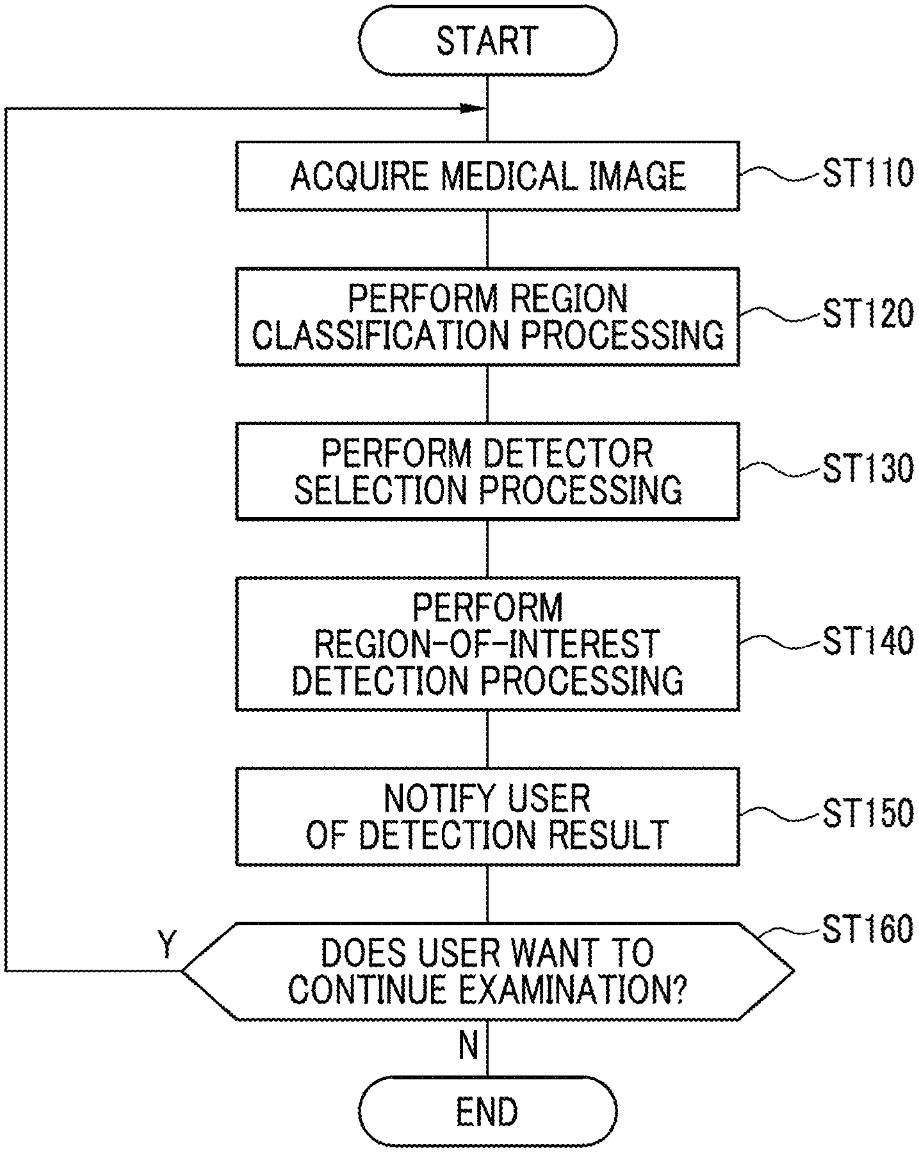
FIG. 8 is a flowchart showing an operation of the medical image processing device.
Figure 9A:
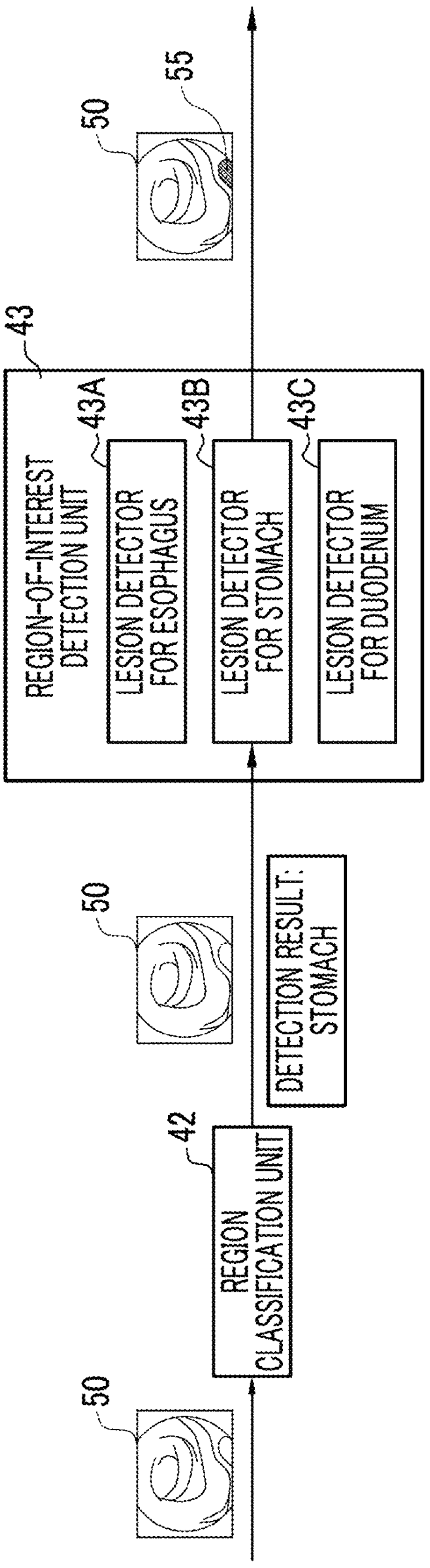
FIGS. 9A and 9B are specific examples of the processing of the region classification unit and the region-of-interest detection unit.
Figure 9B:
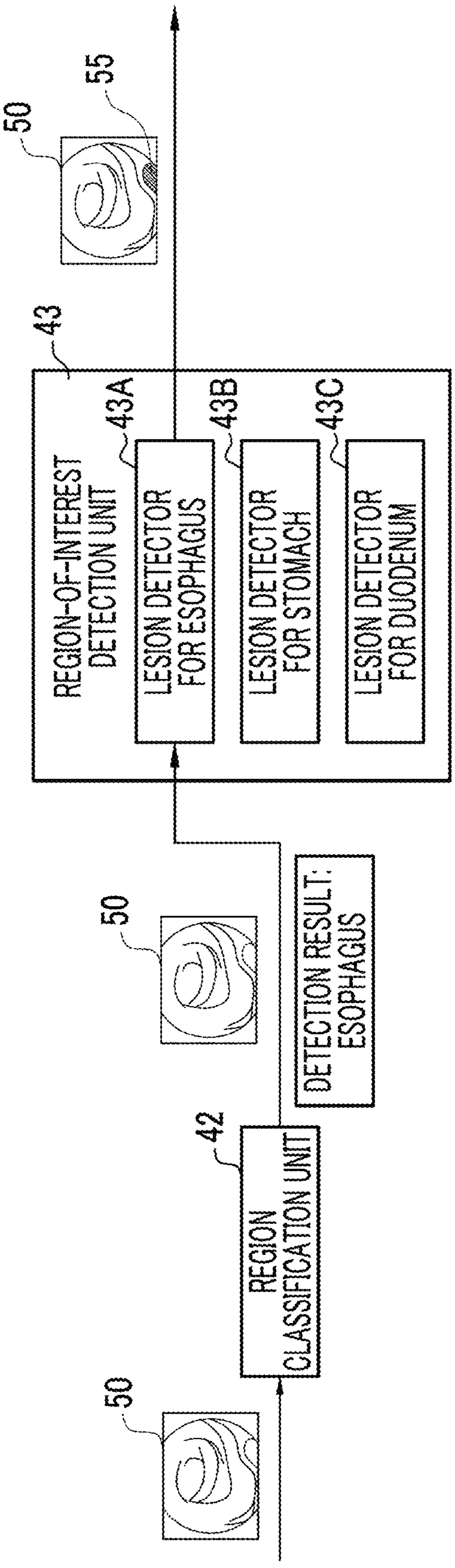

Next, the flow of processing of the medical image processing device 20 in a case where an examination is made using the endoscope system 10 will be described with reference to a flowchart shown in FIG. 8 and diagrams shown in FIGS. 9A and 9B. Examples shown in FIG. 8 and FIGS. 9A and 9B show operations in a case where two modes, that is, the region-of-interest detection mode and the region classification mode are simultaneously executed in the endoscope system 10. A medical doctor who is a user turns on the power of the endoscope system 10 and observes the inside of an examinee. Then, the endoscope system 10 sequentially captures endoscopic images that are medical images 50.

In the medical image processing device 20, first, the medical image acquisition unit 41 acquires a plurality of medical images from the processor device 14 in a time series (Step ST110). Next, the region classification processing for the medical images 50 acquired by the region classification unit 42 is performed (Step ST120). In the present embodiment, the region classification unit 42 performs the region classification processing for classifying a region of a subject in which the medical images 50 are captured into a first region or a second region. Specifically, the region classification unit 42 performs the region classification processing for recognizing which region of the esophagus 101, the stomach 102, or the duodenum 103 is the region of the subject and classifying the region of the subject.

Next, the region-of-interest detection unit 43 performs the detector selection processing for selecting any one of the lesion detector 43A for an esophagus, the lesion detector 43B for a stomach, or the lesion detector 43C for a duodenum, that is, a first trained model or a second trained model using a classification result obtained from the region classification unit 42 (Step ST130). Subsequently, the region-of-interest detection unit 43 performs the region-of-interest detection processing for detecting a region of interest from the medical images 50 by any one of the lesion detector 43A for an esophagus, the lesion detector 43B for a stomach, or the lesion detector 43C for a duodenum, that is, the first trained model or the second trained model which is selected in the detector selection processing (Step ST140).

The display controller 44 and the notification controller 45 notify the user of a detection result of the region of interest on the basis of the detection result of the region of interest obtained from the region-of-interest detection unit 43 and the medical images 50 (Step ST150). In a case where the user wants to continue the examination (Y in Step ST160), the process returns to the acquisition of the medical images 50 using the medical image acquisition unit 41 (Step ST110) and the above-mentioned processing is repeated. In a case where the user wants to end the examination (N in Step ST160), the user turns off the power of the endoscope system 10.

In a case where an examination is made using the endoscope system 10 as described above, a region of a subject may be classified into the second region in the region classification processing performed by the region classification unit 42 even though the first region is actually imaged and the medical images 50 are obtained. For example, with regard to the medical images 50 captured near a boundary of the region of the subject, a false classification result may be generated in the region classification processing performed by the region classification unit 42. Alternatively, a false classification result may be generated in the region classification processing performed by the region classification unit 42 even due to a change in the form of a lumen caused by the peristalsis of a gastrointestinal tract that is a subject, water coverage in a case where liquid or the like is sprayed on the subject, an influence in a case where the imaging optical system of the endoscope 12 is out of focus, or the like. In the example shown in FIG. 4, medical images 50 captured near a boundary 104 between the esophagus 101 and the stomach 102 and near a boundary 105 between the stomach 102 and the duodenum correspond to the medical images 50 captured near the boundary.

As shown in FIG. 9A, in a case where a classification result is the stomach 102, the lesion detector 43B for a stomach is selected by the region-of-interest detection unit 43 and the detection of a region 55 of interest is performed in the medical image 50. On the other hand, as shown in FIG. 9B, in a case where a classification result is the esophagus 101, the lesion detector 43A for an esophagus is selected by the region-of-interest detection unit 43 and the detection of a region 55 of interest is performed in the medical image 50.

In a case where the medical images 50 are captured near the boundaries 104 and 105 as described above, the region classification unit 42 is likely to generate a classification result in which the region of the subject is the esophagus 101 even though, for example, the stomach 102 is actually imaged and the medical images 50 are acquired. In this case, the region-of-interest detection unit 43 selects the lesion detector 43A for an esophagus on the basis of the false classification result.

However, since the first data set DS1 including the data D1 of the first region and the data D2 of the second region is input to the learning unit 46 in the present embodiment, the data D2 of the second region, that is, the data of the stomach are also included in the first data set DS1 that has been used to train the lesion detector 43A for an esophagus. Accordingly, since detection is performed in the medical images 50, which are acquired in a case where the stomach is actually imaged, by the first trained model trained with the first data set DS1 including the data of the stomach, false detection is less caused by the region-of-interest detection unit 43. Further, since the region-of-interest detection unit 43 less detects a region that is actually not a region of interest as the region of interest and less detects an actual region of interest as a region that is not the region of interest, the region-of-interest detection unit 43 can detect a region of interest with a stable behavior.

On the other hand, in a case where the stomach 102 is imaged and the medical images 50 are acquired, the region classification unit 42 almost always generates a correct classification result of the stomach 102. In this case, the lesion detector 43B for a stomach of the region-of-interest detection unit 43 is selected on the basis of the correct classification result and the detection of a region 55 of interest is performed in the medical image 50. In a case where the first region is the esophagus and the second region is the stomach as in the specific example described above, the data of the medical image of the stomach as the second region are included in the second data set DS2 that has been used to train the lesion detector 43B for a stomach. Accordingly, false detection is less caused by the region-of-interest detection unit 43.

Further, in the present embodiment, the first data set DS1 used for deep learning includes the data D1 of the first region more than the data D2 of the second region. For example, in a case where the first region is the esophagus, the data of the esophagus that are the data D1 of the first region are more than the data of the stomach or the duodenum that are the data D2 of the second region. The first trained model generated in this way is the lesion detector 43A for an esophagus. Accordingly, since the detection of a region of interest is performed by the lesion detector 43A for an esophagus trained with the first data set DS1 including a large amount of data of the esophagus in a case where a classification result is the esophagus 101, the region-of-interest detection unit 43 can detect a region of interest with higher accuracy. Therefore, the region-of-interest detection unit 43 can detect a region of interest with a stable behavior.

Second Embodiment

Figure 10:
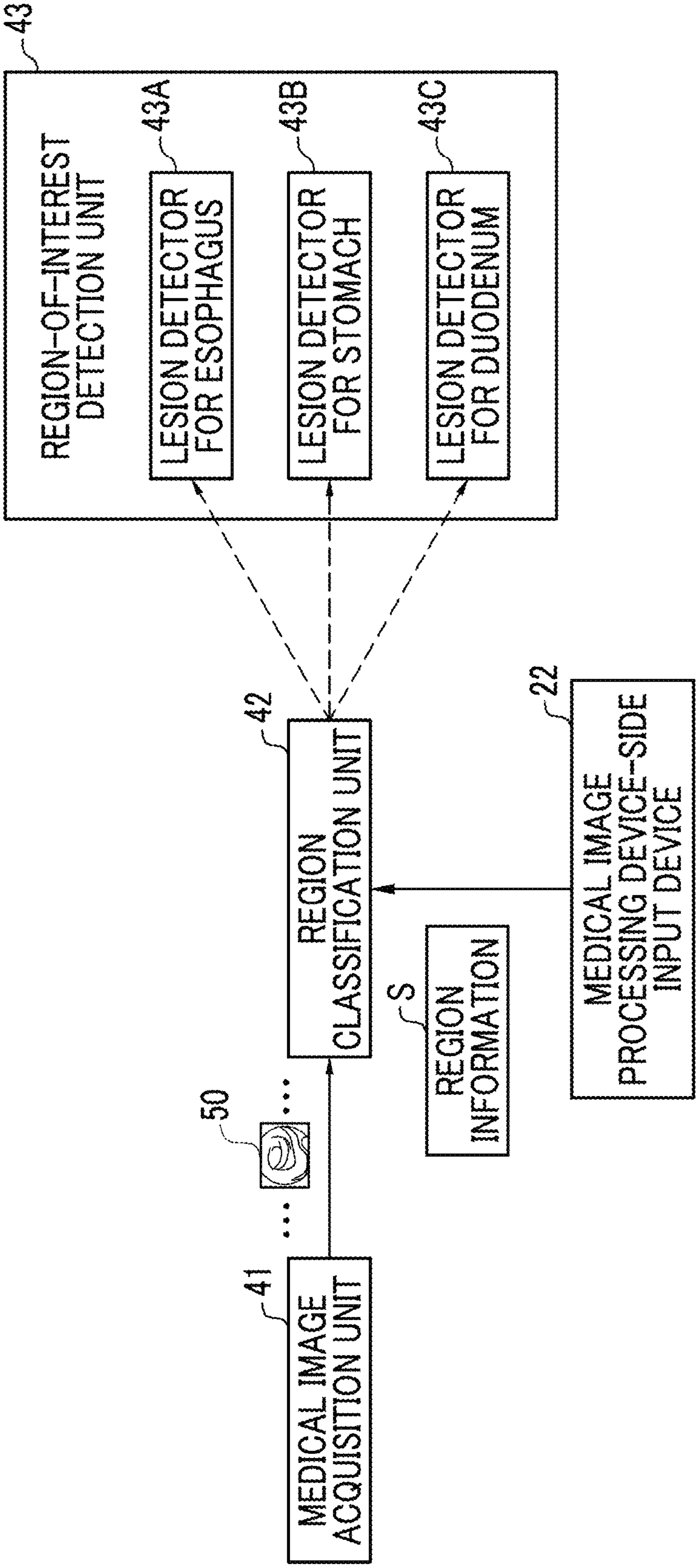
FIG. 10 is a block diagram showing a part of a configuration of a medical image processing device according to a second embodiment.

In the first embodiment, the region classification unit 42 analyzes medical images to acquire a classification result indicating a region of a subject in which the medical images 50 are captured. However, the present invention is not limited thereto, and the region classification unit 42 may acquire a classification result indicating a region of a subject in which medical images 50 are captured on the basis of a user's input as shown in FIG. 10. In this case, for example, the region classification unit 42 receives region information S that is input by a user operating the medical image processing device-side input device 22. Then, the region classification unit 42 uses the region information S, which is input by the user, as a classification result. Since the configuration of a medical image processing device according to the present embodiment is the same as that of the medical image processing device 20 according to the first embodiment except for a region classification unit 42, description thereof will be omitted.

Figure 11:
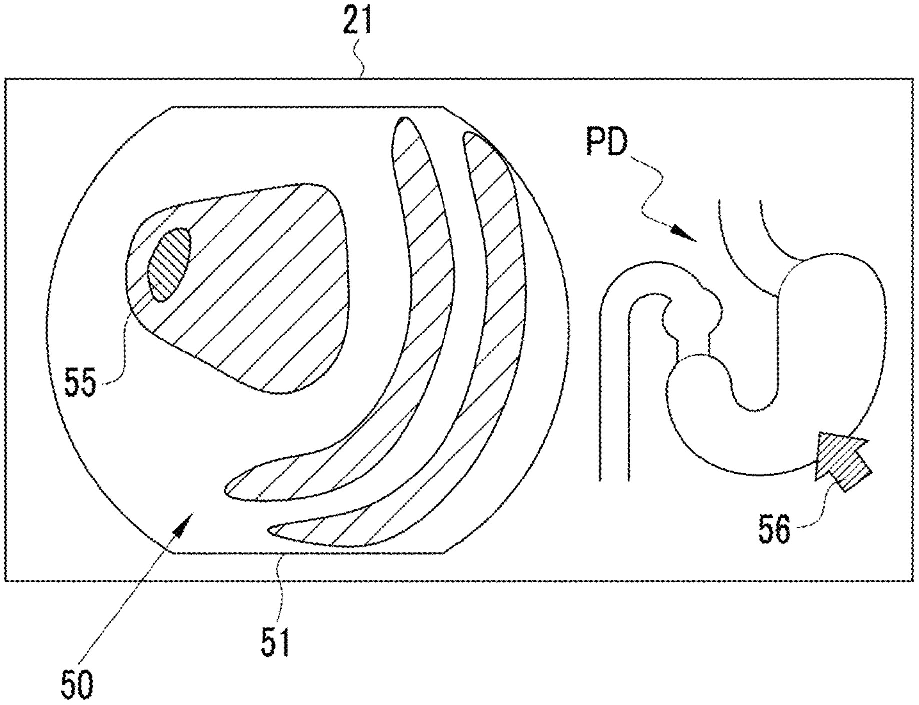
FIG. 11 is an image diagram showing a display screen in a case where the medical image processing device according to the second embodiment receives an input of region information on the basis of a user's operation.

In a case where region information S is input, as shown in, for example, FIG. 11, the medical image display 21 displays a medical image 50 in real time as a video under examination and displays a schematic diagram PD showing the region of the subject. In the example shown in FIG. 11, an esophagus, a stomach, and a duodenum are set as regions of the subject as in the first embodiment. A user operates the medical image processing device-side input device 22 to align the position of a pointer 56 with the position of a region (one of the esophagus, the stomach, or the duodenum) of the schematic diagram PD while observing the medical image 50. Accordingly, the user can input the region information S.

In the flow of processing of the medical image processing device according to the present embodiment, a medical doctor who is a user operates the medical image processing device-side input device 22 to input the region information at the time of the region classification processing (Step ST120; see FIG. 8) of the first embodiment. Then, the region-of-interest detection unit 43 performs detector selection processing for selecting any one of the lesion detector 43A for an esophagus, the lesion detector 43B for a stomach, or the lesion detector 43C for a duodenum using the region information input by the user as a classification result (Step ST130; see FIG. 8). Subsequent processing is the same as that of the first embodiment.

In a case where an examination is made using an endoscope system including the medical image processing device according to the present embodiment as described above, a region of a subject may be classified into a second region due to false region information input by the user even though a first region is actually imaged and medical images 50 are obtained. In particular, since it is difficult to determine the region of the subject with regard to the medical image 50 captured near a boundary of the region of the subject, a false classification result may be generated. Alternatively, since the user forgets to perform an operation during the examination, it may not be possible to switch a classification result to an appropriate classification result.

However, since the first data set DS1 including the data D1 of the first region and the data D2 of the second region is input to the learning unit 46 as in the first embodiment, the data D2 of the second region are also included in the first data set DS1 that has been used to train the first trained model. Accordingly, in a case where the region of the subject is classified into the second region due to false region information input by the user, for example, in a case where the region of a subject is classified into the esophagus on the basis of a user's input with regard to the medical image 50 that is acquired in a case where the stomach is actually imaged, detection is performed by a trained model trained with the first data set DS1 including the data of the stomach. Therefore, false detection is less caused by the region-of-interest detection unit 43. Further, the region-of-interest detection unit 43 can detect a region of interest with a stable behavior as in the first embodiment.

First Modification Example

Figure 12:
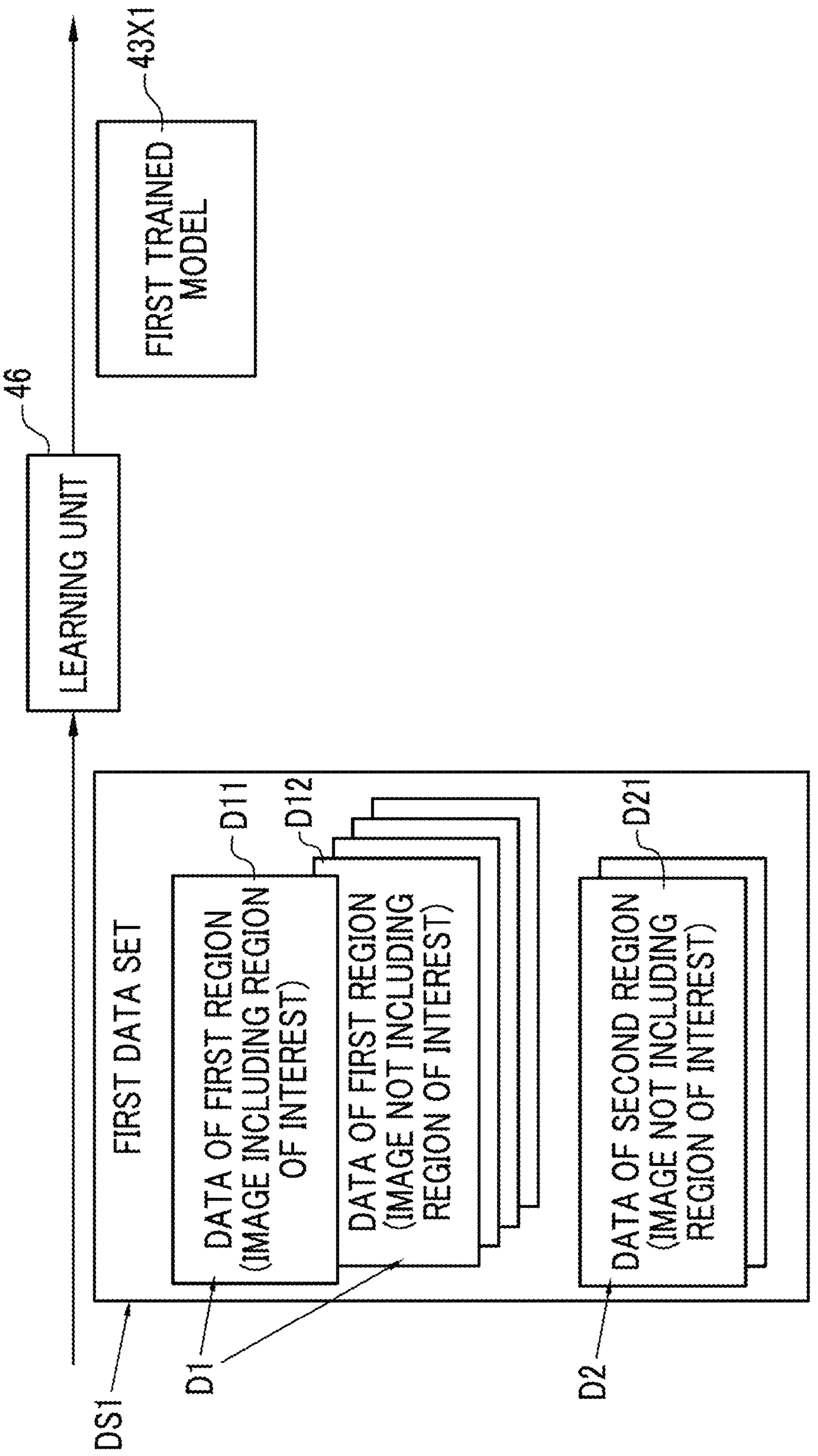
FIG. 12 is a diagram illustrating learning for generating a trained model of a first modification example.

In each embodiment, whether or not to include a region of interest in the data of a data set used for deep learning is not limited. In a modification example shown in FIG. 12, a first data set DS1 is formed of data D1 of a first region that include an image D11 including a region of interest and images D12 not including the region of interest and data D2 of a second region that include images D21 not including the region of interest. Accordingly, since the detection of the region of interest is performed by a first trained model 43X1 trained with the first data set DS1 formed of the image D11 including the region of interest as the data of the first region in a case where a classification result obtained from the region classification unit 42 is the first region, the region-of-interest detection unit 43 can detect the region of interest with higher accuracy. Therefore, the region-of-interest detection unit 43 can detect the region of interest with a stable behavior. In particular, in a case where a medical image 50 of the second region is input to the first trained model, the false detection of the region of interest can be suppressed.

Second Modification Example

In each embodiment and the first modification example, in order to adjust the detection accuracy obtained from the first trained model and the second trained model, the numbers and contents of data D1 and D2 are set to be different in the first data set DS1 and the second data set DS2 used to train the first trained model and the second trained model. However, the present invention is not limited thereto, and the proportion (weighting) of each of the data D1 and D2 may be set to be different at the time of training the models by the learning unit 46 to adjust the detection accuracy of the models. In this case, it is preferable that the proportion of each of the data D1 and D2 is set to be different such that the first trained model has the detection accuracy of the region of interest in the first region higher than detection accuracy of the region of interest in the second region and the second trained model has the detection accuracy of the region of interest in the second region higher than the detection accuracy of the region of interest in the first region.

It is preferable that high detection accuracy in this specification is high sensitivity and/or high specificity. High sensitivity means that a region to be determined as the region of interest is highly likely to be correctly determined as the region of interest, and high specificity means that a region is normal (without the region of interest) and is less likely to be determined as a region including the region of interest.

Third Modification Example

Figure 13:
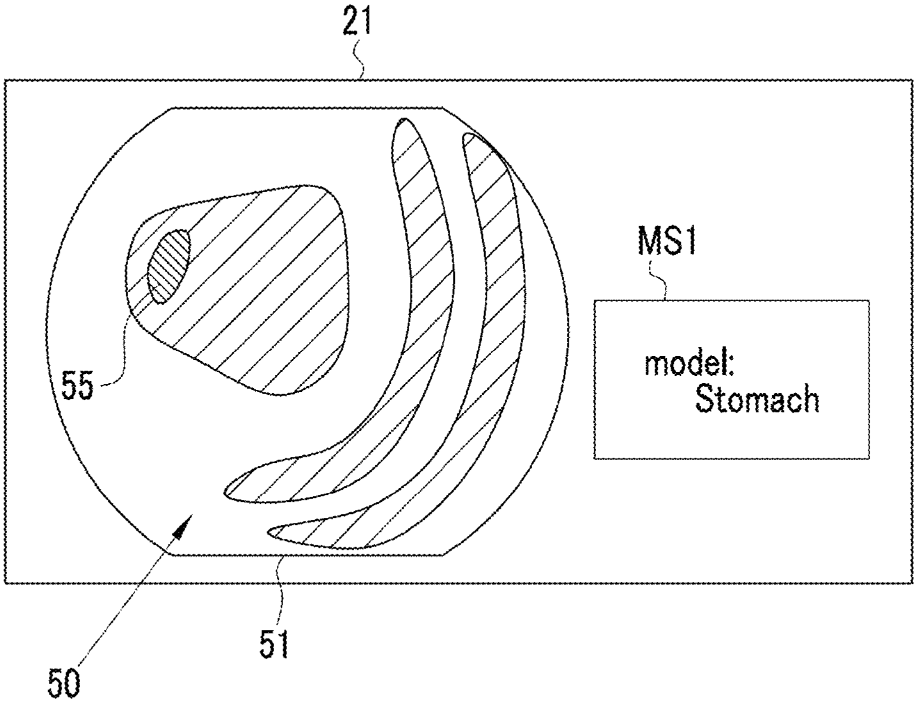
FIG. 13 is an image diagram showing a display screen of a medical image display of a third modification example.

In each embodiment, in a case where the region 55 of interest is detected from the medical images 50 by the region-of-interest detection unit 43, the display controller 44 causes the medical image display 21 to display the medical images 50 in which the region of interest is detected such that the detection result is superimposed on the medical images 50. However, the present invention is not limited thereto, and the display controller 44 may cause the medical image display 21 to display a medical image 50 such that a message MS1 indicating the detection of the region 55 of interest is superimposed on the medical image 50 as shown in FIG. 13. Further, in this way, the selection state of the first trained model or the second trained model selected by the region-of-interest detection unit 43 may be displayed as the message MS1 indicating the detection of the region 55 of interest.

A message MS1 of "Stomach" indicating that the lesion detector 43B for a stomach is selected as the first trained model or the second trained model selected by the region-of-interest detection unit 43 is displayed in the modification example shown in FIG. 13. A display aspect in which the selection state of the first trained model or the second trained model selected by the region-of-interest detection unit 43 is displayed is not limited thereto, and the display controller 44 may cause the medical image display 21 to display the schematic diagram PD, which corresponds to the region of the subject, as the selection state of the first trained model or the second trained model as shown in FIG. 11.

Further, the display controller 44 may cause the medical image display 21 to display not only a display aspect in which the detection result of the region 55 of interest is displayed as in each embodiment but also a message that indicates the selection state of the first trained model or the second trained model as in the modification example shown in FIG. 13. Accordingly, a user can check whether or not the first trained model or the second trained model is correctly selected from the comparison between the selection state of the first trained model or the second trained model and the medical image 50 displayed on the medical image display 21.

The hardware structures of the processing units, which execute various types of processing in each embodiment, such as the medical image acquisition unit, the region classification unit, the region-of-interest detection unit, the display controller, the notification controller, and the learning unit, are various processors to be described below. Various processors include: a central processing unit (CPU) that is a general-purpose processor functioning as various processing units by executing software (programs); a graphical processing unit (GPU); a programmable logic device (PLD) that is a processor of which the circuit configuration can be changed after manufacture, such as a field programmable gate array (FPGA); a dedicated electrical circuit that is a processor having circuit configuration designed exclusively to execute various types of processing; and the like.

One processing unit may be formed of one of these various processors, or may be formed of a combination of two or more processors of the same type or different types (for example, a plurality of FPGAs, a combination of a CPU and an FPGA, a combination of a CPU and a GPU, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, using one integrated circuit (IC) chip as typified by system on chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disc drive (HDD) or a solid state drive (SSD).

Supplementary Claim 1

A medical image processing device comprising a processor, wherein the processor is configured to:

acquire a medical image in which a subject is imaged;

classify a region of the subject of the medical image into a first region or a second region; and detect a region of interest from the medical image using a first trained model obtained from machine learning with a first data set including data of the first region and data of the second region with regard to the medical image of which the region of the subject is classified into the first region, and detect a region of interest from the medical image using a second trained model obtained from machine learning with a second data set including the data of the second region with regard to the medical image of which the region of the subject is classified into the second region, and the first data set includes the data of the first region more than the data of the second region.

Supplementary Claim 2

The medical image processing device according to claim 1, wherein the first trained model has detection accuracy of the region of interest in the first region higher than detection accuracy of the region of interest in the second region, and the second trained model has the detection accuracy of the region of interest in the second region higher than the detection accuracy of the region of interest in the first region.

Supplementary Claim 3

The medical image processing device according to claim 1 or 2, wherein the first data set includes an image including the region of interest and an image not including the region of interest that correspond to the data of the first region and an image not including the region of interest that corresponds to the data of the second region.

Supplementary Claim 4

The medical image processing device according to any one of claims 1 to 3, wherein the first trained model or the second trained model is the trained model trained with data and/or the first data set or the second data set having different combinations of the data.

Supplementary Claim 5

The medical image processing device according to any one of claims 1 to 4, wherein the processor analyzes the medical image to acquire a classification result indicating the region of the subject in which the medical image is captured, and selects the first trained model or the second trained model corresponding to the classification result.

Supplementary Claim 6

The medical image processing device according to any one of claims 1 to 5, wherein the processor acquires a classification result indicating the region of the subject in which the medical image is captured on the basis of a user's input, and selects the first trained model or the second trained model corresponding to the classification result.

Supplementary Claim 7

The medical image processing device according to any one of claims 1 to 6, wherein the processor performs a control of notifying a user of a detection result obtained from the first trained model or the second trained model.

Supplementary Claim 8

The medical image processing device according to claim 7, wherein the processor performs a display control of causing a medical image display to display the acquired time-series medical images, and causes the medical image display to display the medical images in which the region of interest is detected such that the detection result is superimposed on the medical images, for the notification.

Supplementary Claim 9

The medical image processing device according to claim 7, wherein the processor notifies a user of not only the detection result but also a selection state of the first trained model or the second trained model.

Supplementary Claim 10

The medical image processing device according to any one of claims 1 to 9, wherein the machine learning is deep learning.

Supplementary Claim 11

An endoscope system comprising:

an endoscope that captures the medical image; and the medical image processing device according to any one of claims 1 to 10.

Supplementary Claim 12

A method of operating a medical image processing device, comprising:

a step of acquiring a medical image in which a subject is imaged;

a step of classifying a region of the subject in which the medical image is captured into a first region or a second region;

a step of detecting a region of interest from the medical image using a first trained model obtained from machine learning with a first data set including data of the first region and data of the second region with regard to the medical image of which the region of the subject is classified into the first region; and a step of detecting a region of interest from the medical image using a second trained model obtained from machine learning with a second data set including the data of the second region with regard to the medical image of which the region of the subject is classified into the second region, wherein the first data set includes the data of the first region more than the data of the second region.

Supplementary Claim 13

A program for a medical image processing device causing a computer to execute:

processing for acquiring a medical image in which a subject is imaged;

processing for classifying a region of the subject in which the medical image is captured into a first region or a second region;

processing for detecting a region of interest from the medical image using a first trained model obtained from machine learning with a first data set including data of the first region and data of the second region with regard to the medical image of which the region of the subject is classified into the first region; and processing for detecting a region of interest from the medical image using a second trained model obtained from machine learning with a second data set including the data of the second region with regard to the medical image of which the region of the subject is classified into the second region, wherein the first data set includes the data of the first region more than the data of the second region.

EXPLANATION OF REFERENCES

10: endoscope system
12: endoscope
12*a*: insertion part
12*b*: operation part
12*c*: bendable part
12*d*: distal end part
12*e*: angle knob
12*f*: mode selector switch
12*h*: still image acquisition instruction switch
12*i*: zoom operation part
13: light source device
14: processor device
15: display
16: processor device-side input device
19: scope-side input device
20: medical image processing device
21: medical image display
22: medical image processing device-side input device
25: controller
26: communication unit
27: storage unit
28: data bus
29: speaker
30: network
31: CPU (Central Processing Unit)
32: RAM (Random Access Memory)
33: ROM (Read Only Memory)
34: program for medical image processing device
35: data for medical image processing device
35*a*: temporary storage section
35*b*: data storage section
41: medical image acquisition unit
42: region classification unit
43: region-of-interest detection unit
43A: lesion detector for esophagus
43B: lesion detector for stomach
43C: lesion detector for duodenum
43X1: first trained model
43X2: second trained model
44: display controller
45: notification controller
46: learning unit
50: medical image
51: main screen
51A: outer frame
55: region of interest
56: pointer
100: upper gastrointestinal tract
101: esophagus
102: stomach
103: duodenum
104, 105: boundary
D1, D2: data
D11: image including region of interest
D12: image not including region of interest
D21: image not including region of interest
DS1: first data set
DS2: second data set
MS1: message
PD: schematic diagram

What is claimed is:

1. A medical image processing device comprising:

one or more processors configured to:

acquire a medical image in which a subject is imaged;

classify a region of the subject in the medical image into a first region or a second region;

detect a region of interest from the medical image using a first trained model obtained from machine learning with a first data set including data of the first region and data of the second region, with regard to the medical image of which the region of the subject is classified into the first region; and detect a region of interest from the medical image using a second trained model obtained from machine learning with a second data set including data of the second region, with regard to the medical image of which the region of the subject is classified into the second region, and the first data set includes relatively more data of the first region compared to data of the second region.

2. The medical image processing device according to claim 1, wherein the first trained model has a higher detection accuracy for the region of interest in the first region than for the region of interest in the second region, and the second trained model has a higher detection accuracy for the region of interest in the second region than for the region of interest in the first region.

3. The medical image processing device according to claim 1, wherein the first data set is composed of data of the first region which includes images containing the region of interest and images not containing the region of interest, and data of the second region which includes images not containing the region of interest.

4. The medical image processing device according to claim 1, wherein either the first trained model or the second trained model is the trained model trained with either the first data set or the second data set, which differ in data and/or combinations of data.

5. The medical image processing device according to claim 1, wherein the one or more processors configured to analyze the medical image to acquire a classification result indicating the region of the subject in the medical image, and select the first trained model or the second trained model according to the classification result.

6. The medical image processing device according to claim 1, wherein the one or more processors configured to acquire a classification result indicating the region of the subject in the medical image on the basis of a user's input, and select the first trained model or the second trained model according to the classification result.

7. The medical image processing device according to claim 1, wherein the one or more processors configured to perform a control of notifying a user of a detection result obtained from the first trained model or the second trained model.

8. The medical image processing device according to claim 7, wherein the one or more processors configured to perform a display control to display the acquired time-series medical images on a medical image display, and superimpose the detection results onto the medical images in which the region of interest is detected and display the superimposed images on the medical image display, for the notification.

9. The medical image processing device according to claim 7, wherein the one or more processors configured to notify a user of not only the detection result but also a selection state of the first trained model or the second trained model.

10. The medical image processing device according to claim 1, wherein the machine learning is deep learning.

11. An endoscope system comprising:

an endoscope that captures the medical image; and the medical image processing device according to claim 1.

12. A method of operating a medical image processing device, comprising:

a step of acquiring a medical image in which a subject is imaged;

a step of classifying a region of the subject in the medical image into a first region or a second region;

a step of detecting a region of interest from the medical image using a first trained model obtained from machine learning with a first data set including data of the first region and data of the second region, with regard to the medical image of which the region of the subject is classified into the first region; and a step of detecting a region of interest from the medical image using a second trained model obtained from machine learning with a second data set including the data of the second region, with regard to the medical image of which the region of the subject is classified into the second region, wherein the first data set includes relatively more data of the first region compared to data of the second region.

13. A non-transitory computer readable medium for storing a computer-executable program, the computer-executable program causing a computer to execute:

processing for acquiring a medical image in which a subject is imaged;

processing for classifying a region of the subject in the medical image into a first region or a second region;

processing for detecting a region of interest from the medical image using a first trained model obtained from machine learning with a first data set including data of the first region and data of the second region, with regard to the medical image of which the region of the subject is classified into the first region; and processing for detecting a region of interest from the medical image using a second trained model obtained from machine learning with a second data set including the data of the second region, with regard to the medical image of which the region of the subject is classified into the second region, wherein the first data set includes relatively more data of the first region compared to data of the second region.

* * * * *